United States Patent [19]
Rundell et al.

[11] Patent Number: 5,994,078
[45] Date of Patent: *Nov. 30, 1999

[54] STABLE ENCAPSULATED REFERENCE NUCLEIC ACID AND METHOD OF MAKING

[75] Inventors: Clark A. Rundell, Standish; Calvin P. H. Vary, Windham, both of Me.

[73] Assignee: Maine Medical Center, Portland, Me.

[*] Notice: This patent is subject to a terminal disclaimer.

[21] Appl. No.: 08/997,522

[22] Filed: Dec. 23, 1997

Related U.S. Application Data

[63] Continuation-in-part of application No. 08/905,124, Jul. 31, 1997.

[51] Int. Cl.$^6$ .............................. C12Q 1/70; C12Q 1/68; C07H 19/00; C07H 21/02
[52] U.S. Cl. ................................ 435/6; 435/5; 435/440; 536/22.1; 536/23.1; 514/1; 514/44
[58] Field of Search .................................. 435/5, 6, 445; 536/22.1, 23.1; 514/1, 44

[56] References Cited

U.S. PATENT DOCUMENTS

| | | | |
|---|---|---|---|
| 5,478,722 | 12/1995 | Caldwell | 435/1.1 |
| 5,677,124 | 10/1997 | DuBois et al. | 435/5 |

FOREIGN PATENT DOCUMENTS

| | | |
|---|---|---|
| 0336412 | 11/1989 | European Pat. Off. |
| WO 92/14487 | 9/1992 | WIPO |
| WO 96/30546 | 10/1996 | WIPO |
| WO 97/38137 | 10/1997 | WIPO |

OTHER PUBLICATIONS

Rosenstraus, Maurice et al., An Internal Control for Routine Diagnostic PCR: Design, Properties, and Effect on Clinical Performance, Journal of Clinical Microbiology; Jan. 1998 vol. 36, No. J, pp. 191–197.

Pasloske, B. I. et al., Novel ribonuclease resistant RNA standards for HIV diagnostics, Clin. Chem. vol. 42, pp. 1890–1891, 1996.

Vary et al., Allele–Specific Hybridization of Lipoprotein Lipase and Factor–V Leiden Missense Mutations with Direct Label Alkaline Phosphatase—Conjugated Oligonucleotide Probes, Genetic Analysis: Biomolecular Engineering, vol. 13, 1996 pp. 59–65.

Watson et al. DNA cloning vol. 1, 1986 IRL Press, Oxford, Washington DC, pp. 79–88.

Takagi et al., DNA Sequence of Lipoprotien Lipase cDNA Cloned from Human Monocytic Leukemia THP–1 Cells, vol. 18 No. 21, 1990, p. 6436.

Sambrook et al., Molecualr Cloning vol. 1, 1990, Cold Spring Harbour Press, New York pp. 1.7–1.16.

Sambrook et al., Molecular Cloning vol. 3, 1990, Cold Spring Harbour Press, New York, A.5 Storage Media p. A.5.

Shade et al., Nucleotide Sequence and Genome Organization of Human Parvovirus B 19 Isolated from the Serum of a Child during Aplastic Crisis, Journal of Virology, vol. 58, No. 3, pp. 921–936 (Jun. 1, 1986).

Reischl et al., Quantitative PCR A Survey of the Present Technology, Molecular Biotechnology, vol. 3, 1995, pp. 55–71.

*Primary Examiner*—Ardin H. Marschel
*Assistant Examiner*—Jezia Riley
*Attorney, Agent, or Firm*—Wood, Herron & Evans, LLP

[57] ABSTRACT

Stable reference nucleic acid for use in all steps of molecular screening and diagnostic assays and method of making. A desired nucleic acid sequence is amplified, ligated into an expression vector, and used to transform a vehicle. A cellular vehicle is subsequently killed without affecting the encapsulated nucleic acid. The vehicle membrane is stabilized under controlled conditions to a stability substantially matching that of a test cell membrane. The recovered nucleic acid is used as a standard or control in molecular diagnostic and genetic testing assays.

39 Claims, No Drawings

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 201 base pairs
      (B) TYPE: nucleic acid
      (C) STRANDEDNESS: single
      (D) TOPOLOGY: linear (iii) HYPOTHETICAL: NO (iv) ANTI-SENSE: NO (vi) ORIGINAL SOURCE:
      (A) ORGANISM: parvovirus B19
      (B) STRAIN: BL9

(xi) SEQUENCE DESCRIPTION: SEQ ID NO:1:

```
TTCTTTTCAG CTTTTAGGTA CAGGAGGTAC AGCATCTATG TCTTATAAGT TTCCTCCAGT      60

GCCCCCAGAA AATTTAGAGG GCTGCAGTCA ACACTTTTAT GAAATGTACA ATCCCTTATA     120

CGGATCCCGC TTAGGGGTTC CTGACACATT AGGAGGTGAC CCAAAATTTA GATCTTTAAC     180
```

```
ACATGAAGAC CATGCAATTC A                                              201

(2) INFORMATION FOR SEQ ID NO:2:

(i) SEQUENCE CHARACTERISTICS:
        (A) LENGTH: 231 base pairs
        (B) TYPE: nucleic acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: human
        (G) CELL TYPE: lymphocyte (xi) SEQUENCE DESCRIPTION: SEQ ID NO:2:

GGCCTCGATC CAGCTGGACC TAACTTTGAG TATGCAGAAG CCCCGAGTCG TCTTTCTCCT     60

GATGATGCAG ATTTTGTAGA CGTCTTACAC ACATTCACCA GAGGGTCCCC TGGTCGAAGC    120

ATTGGAATCC AGAAACCAGT TGGGCATGTT GACATTTACC CGAATGGAGG TACTTTTCAG    180

CCAGGATGTA ACATTGGAGA AGCTATCCGC GTGATTGCAG AGAGAGGACT T             231

(2) INFORMATION FOR SEQ ID NO:3:

(i) SEQUENCE CHARACTERISTICS:
        (A) LENGTH: 192 base pairs
        (B) TYPE: nucleic acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: human
        (G) CELL TYPE: lymphocyte (xi) SEQUENCE DESCRIPTION: SEQ ID NO:3:

ACATCGCCTC TGGGCTAATA GGACTACTTC TAATCTGTAA GAGCAGATCC CTGGACAGGC     60

GAGGAATACA GGTATTTTGT CCTTGAAGTA ACCTTTCAGA AATTCTGAGA ATTTCTTCTG    120

GCTAGAACAT GTTAGGTCTC CTGGCTAAAT AATGGGGCAT TTCCTTCAAG AGAACAGTAA    180

TTGTCAATAT CC                                                        192

(2) INFORMATION FOR SEQ ID NO:4:

(i) SEQUENCE CHARACTERISTICS:
        (A) LENGTH: 188 base pairs
        (B) TYPE: nucleic acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: Chlamydia trachomatis
        (B) STRAIN: A (xi) SEQUENCE DESCRIPTION: SEQ ID NO:4:

GGGATTTGAT TTTACGAGAG AGATTTGCAA CTCTTGGTGG TAGACTTTGC AACTCTTGGT     60

GGTAGACTTT GCAACTCTTG GTGGTAGACT TTGCAACTCT TGGTGGTAGA CTTGGTCATA    120
```

-continued

```
ATGGACTTTT GTTGAAAAAT TTCTTAAAAT CTTAGAGCTC CGATTTTGAA TAGCTTTGGT    180

TAAGAAAA                                                              188
```

(2) INFORMATION FOR SEQ ID NO:5:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (iii) HYPOTHETICAL: NO (iv) ANTI-SENSE: NO (vi) ORIGINAL SOURCE:
        (A) ORGANISM: human
        (G) CELL TYPE: lymphocyte (xi) SEQUENCE DESCRIPTION: SEQ ID NO:5:

```
CTCTCCTCAT CCTTCCTCTT TCCTGTCAAG TGCCTCCTTT GGTGAAGGTG ACACATCATG     60

TGACCTCTTC AGTGACCACT CTACGGTGTC GGGCCTTGAA CTACTACCCC CAGAACATCA    120

CCATGAAGTG GCTGAAGGAT AAGCAGCCAA TGGATGCCAA GGAGTTCGAA CCTAAAGACG    180

TATTGCCCAA TGGGGATGGG ACCTACCAGG GCTGGATAAC CTTGGCTGTA CCCCCTGGGG    240

AAGAGCAGAG ATATACGTGC CAGGTGGAGC ACCCAGGCCT GGATCAGCCC CTCATTGTGA    300

TCTGGGGTAT GTGACTGATG AGAGCCAGGA GCTGAGAAAA TCTATTGGGG GTTGAGAGGA    360
```

STABLE ENCAPSULATED REFERENCE NUCLEIC ACID AND METHOD OF MAKING

This is a Continuation-in-Part of application Ser. No. 08/905,124, filed Jul. 31, 1997.

FIELD OF THE INVENTION

This invention is directed to stable reference nucleic acids for use in all phases of molecular diagnostic and genetic assays, and methods of making stable encapsulated reference nucleic acids.

BACKGROUND OF THE INVENTION

Nucleic acids encompass both deoxyribonucleic acid (DNA) and ribonucleic acid (RNA). DNA, present in all nucleated cells, carries the information needed to direct the synthesis of every protein in the body. A single alteration in the correct sequence of the four DNA bases (adenine, thymine, guanine, and cytosine) may result in a defective protein. Depending upon the protein and the affected organism, the defect may range from inconsequential to life-threatening, or may be of intermediate severity. Diseases as diverse as cystic fibrosis, some types of cancer, sickle cell anemia, and atherosclerosis are known to result from specific genetic alterations. RNA, the intermediary between DNA and protein, is the product of transcription of a DNA template. RNA assays are being performed with increasing frequency in research and clinical laboratories. This is due at least in part to the prevalence of RNA viruses such as the human immunodeficiency virus (HIV) that causes AIDS and the hepatitis C virus (HCV), and the development of drugs used in treating infections with RNA viruses.

Nucleic acid assays are routinely performed, either manually or by automated instrumentation, in numerous reference and clinical laboratories. A nucleic acid assay may be performed to detect the presence of foreign DNA or RNA, which may indicate infection with a foreign organism. For example, a variety of molecular assays are used to establish the presence and identity of nucleic acids from the Human Immunodeficiency Virus-1 (HIV-1), Chlamydia, and other organisms causing sexually transmitted diseases. An individual's DNA may also be analyzed to detect, treat, and in some cases prevent genetic disease. Genotype determination of genes for Factor-V Leiden, hereditary hemochromatosis, lipoprotein lipase mutations, and cystic fibrosis have important implications for health management. The Human Genome Project holds the promise of many more examples of medically efficacious genetic diagnostic determinations. The recent discovery of the breast cancer associated gene (BRCA-1) has highlighted both the importance of screening individuals for predisposition to a disease, and also the attendant need for accurate, precise, reproducible, and controlled nucleic acid assays.

Laboratories that perform clinical assays must meet federal and state accrediting agencies' requirements for quality control tests in order to obtain and maintain accreditation. For example, the National Committee for Clinical Laboratory Standards (NCCLS) specifies that quality control samples must be analyzed during every batch of patient specimens analyzed. The federal Clinical Laboratory Improvement Act of 1988 (CLIA'88) mandates similar requirements, as do inspection agencies from most states. The College of American Pathologists (CAP), a non-profit peer inspection group, also requires that quality control samples be analyzed during each analytical run.

In the field of molecular pathology and genetic testing, a quality control sample includes a reference DNA or reference RNA of known quantity and quality to evaluate the reliability of all steps of a test. Such reference nucleic acid is ideally as similar as possible to the test sample, and also has broad applicability to all sample preparation and test formats. Additionally, the reference nucleic acid should be easily produced, quantitated, and packaged with minimal technical capability.

Materials meeting these requirements, however, are lacking in the field of molecular pathology and genetic testing. This is due in large part to the variety of different technologies and techniques currently employed for a given diagnostic determination. For example, genetic determinations currently include the use of the polymerase chain reaction (PCR), the ligase chain reaction (LCR), branched DNA, allele specific hybridization, and direct sequence determination. In addition, so-called "home brew" produced primer oligonucleotides, and isotopically labeled or non-radioisotopic based probes are used in a variety of configurations in genetic testing, but without any systematic quality control materials, and hence without any validation. The aforementioned factors, coupled with the lability of nucleic acids, make it virtually impossible to obtain standard reagents to qualitatively and/or quantitatively assess the overall accuracy, reliability, and efficiency of the numerous manipulations performed in all phases of a laboratory assay, that is, from sample preparation through diagnostic determination. For example, one commercially available material for use as a control in a DNA assay consists of lyophilized DNA powder to be diluted and used beginning at an amplification step, which is late in the protocol and well after sample preparation. Thus, for the steps preceding amplification there is no reference DNA by which the accuracy, reliability, and efficiency of these steps may be evaluated. An additional drawback in the use of this material is the apparent lack of extraneous nucleotide residues and other milieu representative of that which is found in normal cellular extracts.

Even a single alteration in the base sequence of a nucleic acid may have severe consequences to a patient undergoing diagnosis of a genetic disease. Because of the importance of such assays, and also because of the wide range and large numbers of molecular diagnostic assays performed, there is a great need for stable reference nucleic acids to monitor test conditions as closely as possible.

SUMMARY OF THE INVENTION

This invention is directed to a method for biologically preparing a stable encapsulated reference nucleic acid to monitor molecular diagnostic and genetic testing of a test cell. A vector bearing a nucleic acid construct is inserted into a cell through its outer membrane, the cell is killed without affecting the nucleic acid, and the outer membrane stability is matched with the membrane stability of the test cells to stably encapsulate the reference nucleic acid contained therein.

In a preferred embodiment, the vector is a plasmid bearing a reference DNA containing a unique signature mutation that is inserted in an *Escherichia coli* bacterial cell vehicle. The vehicle is propagated and quantitated to determine the concentration of nucleic acid. The cell is killed without affecting the encapsulated reference nucleic acid. Killing may occur by exposure to ambient temperature, a chemical agent, a chemical crosslinker, a chemical carcinogen, a radiation source, or a combination of these. The membrane protein may then be crosslinked under controlled conditions so as to achieve a desired stability of the capsule containing the reference nucleic acid for substantially matching the membrane stability of the test cells. Alternatively, the membrane protein may be crosslinked before the cell is killed without affecting the encapsulated reference nucleic acid, or the membrane protein may not be crosslinked. The concentration of crosslinker is dependent upon the nature of the patient sample and on the specific test to be performed. In particular embodiments, the crosslinker may be glutaraldehyde, formaldehyde, disuccinimidyl suberate, or mixtures thereof, or other agents of this nature, that may crosslink and/or kill cells. In one embodiment, the encapsulated reference nucleic acid is suspended in the test sample matrix. The stabilized encapsulated reference nucleic acid is used in parallel with a test specimen throughout an assay.

This invention is also directed to a method of producing a class of stable encapsulated reference nucleic acid constructs. In preferred embodiments, the class includes nucleic acids from Parvovirus B-19 SEQ ID NO:1, a lipoprotein lipase gene SEQ ID NO:2, a Leiden Factor V mutant SEQ ID NO:3, *Chlamydia trachomatis* SEQ ID NO:4, a hereditary hemochromoatosis candidate gene SEQ ID NO:5, and HIV and HCV diagnostic sequences.

This invention is also directed to a method of preparing a reference nucleic acid encapsulated in a noncellular membrane whose stability matches the membrane stability of a test cell. In different embodiments, the noncellular membrane may be a liposome, a paraffin block, or an agarose capsule, and the membrane may contain protein which may be crosslinked.

The stabilized encapsulated reference nucleic acid constructs having a membrane stability that substantially matches the membrane stability of test cells and produced by the methods of the present invention, are applicable to substantially all sample preparation and test formats, are easily produced in a form analogous to that found in a test specimen, and can be stably maintained when stored under routine laboratory conditions.

By virtue of the foregoing, there is thus provided reference nucleic acid that is stable, broadly applicable for use to monitor all steps of nucleic acid preparations and assays, and is easily manufactured and maintained. These and other objects and advantages of the present invention shall be made apparent from the following description and examples.

DETAILED DESCRIPTION

Definitions

"Reference nucleic acid" encompasses all DNA and RNA used for validation, standardization, quality control, and quality assurance purposes in molecular screening and diagnostic assays in manual, automated, kit and non-kit forms, and includes standards, controls, and calibrators.

"Expression vector" encompasses non-chromosomal double-stranded DNA comprising a complete replicon.

"Recombinant vector" encompasses an expression vector containing exogenous nucleic acid inserted therein.

"Transformation" encompasses the process of placing a vector within a prokaryotic cell.

"Target nucleic acid" encompasses DNA and RNA having a base sequence containing a target sequence to be analyzed in the test specimen.

"Marker gene" encompasses a gene in an expression vector that is situated close to target DNA whereby expression of the marker gene indicates the insertion of the target DNA in the expression vector.

"Nucleic acid construct" encompasses DNA and RNA sequences encoding the particular gene or gene fragment desired, whether obtained by genomic or synthetic methods.

Nucleic Acid Preparation

A DNA or RNA fragment of interest, or equivalently, the base sequence for which the patient sample is being assayed, is obtained using standard molecular biology techniques and protocols knowledgeable to one skilled in the art. Such techniques will not be repeated herein but are set forth in detail in *Molecular Cloning—A Laboratory Manual Second Edition*, J. Sambrook et al., eds, Cold Spring Harbor Laboratory Press, New York (1989), the disclosure of which is hereby incorporated by reference. A DNA fragment of interest may be custom-synthesized using a variety of commercially available methods and instruments known to one skilled in the art.

In a preferred embodiment, oligonucleotides are synthesized by the b-cyanoethylphosphoramidite method using an Applied Biosystems Inc. Model 392 DNA synthesizer (Applied Biosystems). A plurality of 3'-aminoalkyl-derivatized oligonucleotides are prepared using a controlled pore glass support bearing an amino functional group (Clontech Inc.). Oligonucleotides are redissolved in an appropriate volume of diethylpyrocarbonate (DEPC)-treated water. A DNA fragment may also be obtained by nuclease cleavage of genomic DNA using standard molecular biology protocols. Still another way to obtain a DNA fragment is to form a complementary DNA (cDNA) by reverse transcription of messenger ribonucleic acid (mRNA) using standard molecular biology protocols or any in vitro amplification of a DNA fragment. An RNA molecule may be obtained by transcription of an appropriate DNA fragment.

Nucleic Acid Encapsulation

The desired DNA or RNA sequence construct, termed target nucleic acid, is amplified to obtain multiple copies by standard techniques knowledgeable to one skilled in the art. Examples of amplification techniques for DNA are the polymerase chain reaction and the ligase chain reaction.

Amplified target DNA, now present in multiple copies, is put into a form whereby it may be replicated, i.e., located downstream of a promoter and/or enhancer, have the appropriate nucleotides available, and so on. The target DNA is thus ligated into a self-replicating genetic element that serves as an expression vector. In a preferred embodiment, the expression vector is a plasmid such as pBR322 or pGEM-T. In an alternative embodiment, the expression vector is a virus such as M13, Qβ, φX174, lambda phage or other bacteriophage, a portion of a virus, or any other self-replicating system which allows for expression of the target DNA introduced into the viral nucleic acid. The vector preferably contains a marker gene for determining if the target DNA was successfully ligated into the vector. In one embodiment, the marker gene encodes a protein that confers antibiotic resistance, such as an ampicillin resistance gene. When transformed bacteria, containing a marker gene encoding an ampicillin resistance gene, are cultured on media that contain ampicillin, the bacterial colonies capable of growth are those that contain an insert of the target DNA construct. This indicates insertion of target DNA along with the ampicillin resistance gene, which rendered the bacteria immune to the effects of the antibiotic ampicillin.

The plasmid or viral vector containing the target DNA sequence is inserted into a vehicle, which is then said to be transformed. Preferably the transformed vehicle is a prokaryotic or eukaryotic cell from which the plasmid containing the DNA insert can be readily propagated. Most preferably, the bacterium Escherichia coli (E. coli) is the propagation vehicle since it is easily obtained and fulfills federal standards for recombinant material. Any similar bacteria that is easily propagated, however, is acceptable as a vehicle. In one embodiment, the vectors may be a first vector bearing a reference DNA and a second identical vector bearing a second nonidentical reference DNA, and the number of identical vectors per transformed vehicle ranges from about one to about one thousand. In an alternate embodiment, the vectors may be a first vector bearing a reference DNA and a second nonidentical vector bearing a second nonidentical reference DNA, and the number of nonidentical vectors per transformed vehicle ranges from about two to about four. In another alternate embodiment, a vector may bear at least two nonidentical reference DNAs, and the number of nonidentical reference DNAs per vector ranges from about two to about twenty.

One method of transforming a cell is by electroporation but other methods, such as calcium chloride-mediated transformation, are also known to one skilled in the art. An advantage of using bacterial transformation is that the bacteria serve both as an encapsulation means and a propagation means for the target nucleic acid. While prokaryotic cells are commonly used as vehicles to propagate nucleic acid, a eukaryotic cell may also be used. Likewise, other non-cellular encapsulation means are available. For example, DNA may be stably encapsulated in non-cellular capsules such as liposomes, paraffin blocks, or agarose capsules.

The cellular vehicle is propagated by standard culturing techniques known to one skilled in the art. Clones of the nucleic acid are thereby generated in a stable encapsulated form.

Encapsulated Nucleic Acid Stabilization

Nucleic acid that has been ligated into a vector and transformed into E. coli mimics the intracellular conditions in which nucleic acid is routinely found. In one embodiment a cellular vehicle, preferably a bacterial cell containing a plasmid which, in turn, contains the target construct, is killed without affecting the encapsulated reference nucleic acid. The cell wall or membrane of the killed cell may be subsequently stabilized by crosslinking the membrane protein. In another embodiment a cell wall or membrane, preferably a bacterial cell containing a plasmid which, in turn, contains the target construct, is stabilized by crosslinking the membrane protein. The cellular vehicle is subsequently killed without affecting the encapsulated reference nucleic acid. In still another embodiment, the cell wall or membrane may not be crosslinked.

Killing of the cellular vehicle may be accomplished by any method that will not affect the encapsulated reference nucleic acid. Killing may occur by altering a cell's physical or chemical environment, including exposing the cell to an ambient temperature, a chemical agent, a chemical crosslinker, a chemical carcinogen, and/or a radiation source, altering cellular pH, altering the cell wall or membrane, and perturbing cellular respiration. In one embodiment, the E. coli are suspended in buffered 10% formalin solution containing methanol at a concentration of about 1%, and formaldehyde at a concentration of about 4%, or mixtures thereof, in a 0.01 M to 0.5 M phosphate buffer, pH 6.8–7.6. The killed bacteria are then resuspended in phosphate buffered saline (PBS) solution containing a preservative such as ProClin 300® (Supelco). Alternatively, the E. coli are exposed to an ambient temperature sufficient to cause cell death.

Stabilization may occur by crosslinking the proteins in the cell wall or membrane. This permits the target nucleic acid to be stably encased within the cell for extended storage. A stabilized cell wall or membrane prevents premature cell breakage with subsequent release of the vector containing the target nucleic acid. An additional benefit of crosslinking the cell wall or membrane encapsulating a target nucleic acid is to shield the nucleic acid from nucleases or proteases that may otherwise degrade it.

The cellular wall or membrane may be crosslinked in a controlled manner to achieve a membrane stability that substantially matches the membrane stability of the test cells. Crosslinkers known to one skilled in the art are added to cells transformed with an expression vector containing the target nucleic acid construct. Chemical crosslinking agents, for example formaldehyde, glutaraldehyde, and disuccinimidyl suberate are added in a desired concentration selected for the particular assay. Typical concentrations are in the range of about 0.1 mM to about 10 mM for a time appropriate to achieve the degree of crosslinking required for substantially matching with the membrane of the test cells. Any excess crosslinker is removed by washing the bacterial suspension with a PBS solution, followed by centrifuging and resuspending the resultant pellet, typically in a PBS solution containing a preservative such as ProClin 300®.

The reference nucleic acid can be stored in desired quantities under routine laboratory conditions. For example, cells containing DNA or RNA may be lyophilized and stored in vials at 2° C. to 8° C. Alternatively, in one embodiment, the cells may be stored in vials in an imidazole/saline buffer, pH 7.4. The killed and stabilized cells are diluted to achieve a concentration to provide an appropriate signal in the particular assay system to be used.

EXAMPLE 1

Parvovirus B-19 SEQ ID NO:1 is determined by a single-tube nested PCR assay. Outer primers are supplied at a concentration of 0.04 $\mu$M and inner PCR primers are supplied at a concentration of 0.4 $\mu$M. Thermal cycling is performed in a Perkin Elmer thermal cycler, model 2400. Cycling parameters are as follows: 20 cycles of 94° C. for 30 seconds, 50° C. for 30 seconds, 72° C. for 30 seconds, followed by 35 cycles of 94° C. for 30 seconds, 60° C. for 30 seconds, 72° C. for 30 seconds.

Probe-labeled oligonucleotides are synthesized by the b-cyanoethylphosphoramidite method using an Applied Biosystems Inc. Model 392 DNA synthesizer (Applied Biosystems). A plurality of 3'-aminoalkyl-derivatized oligonucleotides (for alkaline phosphatase conjugation) are prepared using a controlled pore glass support bearing an amino functional group (Clontech Inc.). Oligonucleotide PCR primers are redissolved in an appropriate volume of diethylpyrocarbonate (DEPC)-treated water. The 3'-aminoalkyl-derivatized oligonucleotides (100 nmoles) in 0.10 M bicine buffer, pH 8.2, containing 0.15 M NaCl, are reacted with succinimidyl 4-(N-maleimidomethyl)cyclohexane-1-carboxylate (1 $\mu$mole) for ten minutes at room temperature. The maleimidoyl-oligonucleotide is purified using a PD-10 column (Pharmacia Inc.) equilibrated with 1 M NaCl in 0.1 M phosphate buffer pH 7.5. Alkaline phosphatase (71 nmoles, Boehringer-Mannheim) is reacted with N-succinimidyl 3-(2-pyridyldithio)propionate (350 nmoles) in 3 M NaCl in 0.1 M phosphate buffer (pH 7.5) for 30 minutes at room temperature. Modified alkaline phosphatase preparations are desalted using a PD-10 column (Pharmacia Inc.) equilibrated with 1 M NaCl in 0.1 M phosphate, 0.1 M triethylamine buffer (pH 7.5). Following reduction of the pyridyldithiol linkage with dithiothreitol (500 nmoles), the thiolated alkaline phosphatase is desalted on a PD-10 column as described above. The maleimidoyl-oligonucleotide and the thiolated alkaline phosphatase are combined and allowed to react for 16 hours at room temperature.

The PCR products are probed for a sequence specific to Parvovirus B-19 SEQ ID NO:1 using the alkaline phosphatase labeled oligonucleotides in a dot blot hybridization assay. The PCR products are applied to a SurBlot membrane (Oncor), which is placed in 0.2 N NaOH for 5 minutes. The membrane is blocked by incubating with Cool Glow Blocking buffer (0.2% I-Block by Tropix, 0.5% sodium dodecyl sulfate (SDS) in PBS) for 30 minutes. The blocking buffer is replaced by the Parvovirus probe diluted in Cool Glow Blocking buffer. The membrane is incubated with the probe at 53° C. for 30 minutes. The probe solution is removed and the membrane is washed twice with Cool Glow Washing buffer, 0.5% SDS in PBS. The membrane is prepared for staining by two room temperature incubations with a buffer of 0.1 M diethylamine and 1.0 mM $MgCl_2$. The membrane is then covered with a solution of 0.125 mM CSPD (Tropix) for 5 minutes. The CSPD is removed, the membrane is air dried, wrapped in plastic, and exposed to film for 10–30 minutes.

PCR products from a positive sample are purified using Promega's Wizard PCR Preps DNA Purification System. The pGEM-T Vector system is used to insert the Parvovirus sequence SEQ ID NO:1 into the pGEM-T plasmid. The ligation product is ammonium precipitated and then transformed into electrocompetent *E. coli*, strain TOP10F!, by electroporation. Recombinant colonies are screened by transferring a portion of the colony into a tube containing Parvovirus PCR reagents. Detection of the target sequence SEQ ID NO:1 is determined by performing the Parvovirus PCR assay and dot blot hybridization as previously described. Presence of the target sequence SEQ ID NO:1 is confirmed by isolating the plasmid DNA using Promega's Wizard Plus Miniprep DNA Purification System and subsequently performing dye terminator cycle sequencing. Cycle sequencing employs the FS variant of *Thermus aquaticus* DNA polymerase (Perkin-Elmer/Applied Biosystems). Primers are identical to those used in the original PCR assay, but at a concentration of 3.2 pmol. Cycling parameters are as follows: 25 cycles of 96° C. for 10 seconds, 50° C. for 5 seconds, 60° C. for 4 minutes. Thermal cycling is performed in a Perkin-Elmer Thermal Cycler, model 2400. The cycle sequenced reactions are then added to tubes containing 50 $\mu$l of ethanol and 2 $\mu$l of 3 M sodium acetate, incubated for 10 minutes on ice, and centrifuged for 15 minutes at more than 3000 but less than 10,000×g. The supernatant is removed and the pellet is washed with 70% ethanol and dried. The pellet is resuspended in Template Suppression Reagent (Perkin-Elmer/Applied Biosystems) and heated for 2 minutes at 95° C. Samples are then subjected to automated DNA sequence analysis on an AB1 -310 prism DNA sequencer. Analysis of known samples is used to continually assess data accuracy. Data analysis is conducted using on-board software as well as DNA analytical tools on the Internet.

Clones containing the target sequence SEQ ID NO:1 are propagated by growing each clone overnight in LB/ampicillin broth. The culture is mixed with glycerol to 15–50% and frozen in aliquots at −70° C.

Control material is produced by removing aliquots of frozen clones containing the target sequence SEQ ID NO:1 and growing overnight in 3 ml of LB/ampicillin broth. A 1:100 dilution of the culture is made by pipetting 0.2 ml of the overnight culture into 20 ml of LB/ampicillin broth, then the mixture is incubated on a shaker at 37° C. for several hours until late log phase growth is achieved. The culture is centrifuged for 20 minutes at greater than 3000 but less than 10,000×g and the supernatant decanted. The pelleted cells are resuspended in 20 ml of buffered 10% formalin and incubated at room temperature for a minimum of 2 hours. The cells are again pelleted by centrifugation and washed with 20 ml PBS, pH 7.4. The washed cell pellet is resuspended in PBS to a concentration appropriate for the assay in which the control is to be used. For example, the cells containing the parvovirus DNA-containing plasmid sequence SEQ ID NO:1 are diluted with PBS to an optical density at 600 nm ($OD_{600}$)=0.100. ProClin 300® is added to a concentration of 0.04%. Working solutions of the control material are made by diluting the PBS cell suspensions with 0.017 M imidazole/NaCl, pH 7.4.

Bacterial counting is performed, for example, according to the hydrophobic grid membrane filter method as described by the Association of Official Analytical Chemists, on a particle counter such as a Coulter Model ZM using methods according to manufacturer's recommendations, or using a clinical hemocytometer.

Bacterial killing is accomplished by adding about 5–50% ethanol, about 0.01–10% hypochlorite, or mixtures of about 5–50% hypochlorite and about 0.01–10% ethanol to a log phase cell suspension. Fixation is accomplished by adding about 1–10 % formaldehyde or about 1–10% glutaraldehyde. Ideally, less than 1 in $10^6$ viable organisms remain after the killing and fixing treatment. To assess completeness of killing, organisms from each aliquot are incubated in culture media overnight using standard techniques.

Aliquots showing no growth from culture of $10^6$ organisms are washed free of excess chemical additives and tested for preservation of DNA and utility in molecular assays, using nucleic acid amplification such as PCR, LCR, branched DNA or other probe techniques known to one skilled in the art. These assays may be separate from or identical to the clinical assays described above.

EXAMPLE 2

Lipoprotein lipase (LPL) point mutation G188E can be determined by PCR of LPL exon 5 SEQ ID NO:2 from human genomic DNA, followed by dot blot hybridization with alkaline phosphatase labeled probes. PCR is performed in a Perkin Elmer Thermal Cycler, model 2400. Cycling parameters are as follows: hold at 92° C. for 10 minutes, 30 cycles of 94° C. for 30 seconds, 50° C. for 30 seconds, 72° C. for 30 seconds. PCR products are applied to an Oncor membrane, which is then treated with 0.2 N NaOH for 5 minutes. Membranes are blocked with Cool Glow Blocking Buffer (0.2% I-Block by Tropix, 0.5% sodium dodecyl sulfate (SDS) in PBS) at 50° C. for 30 minutes. The blocking buffer is removed and the membrane is hybridized with the LPL 188 probe (prepared as described in Example 1) diluted in Cool Glow Blocking Buffer at 50° C. for 30 minutes. After 30 minutes the conjugate is washed off with Cool Glow Washing Buffer. The membrane is then prepared for staining by two consecutive 5 minute incubations in CSPD buffer (0.1 M diethylamine, 1 mM $MgCl_2$). The membrane is covered with 0.125 mM CSPD (Tropix) for 5 minutes. The substrate is then removed and the membrane is air dried and wrapped in plastic and exposed to film for 1–2 hours.

The PCR product SEQ ID NO:2 is purified using Promega's Wizard PCR Prep DNA Purification System. Ten to fifty pmol are placed into new PCR amplification mixture composed of the appropriate primers and supplementary materials as described in *Molecular Cloning—A Laboratory Manual Second Edition,* J. Sambrook et al., eds, Cold Spring Harbor Laboratory Press, New York (1989). Each product to be amplified is in the presence of one unmodified primer and one modified "mutating" primer, both supplied at 0.4 µM–0.8 µM. Amplification proceeds according to standard PCR protocols. The resulting modified PCR products are cloned as described in Example 1. Recombinant colonies are screened by transferring a portion of the colony into a tube containing LPL188 PCR reagents and performing the LPL PCR assay and dot blot hybridization. Presence of the target sequence SEQ ID NO:2 is confirmed by automated sequencing on the ABI Prism 310 Genetic Analyzer as described in the Parvovirus example.

EXAMPLE 3

Target sequences for Leiden Factor V SEQ ID NO:3 are determined from the literature or empirically using various techniques known to one skilled in the art including PCR, gel electrophoresis, and sequencing. Oligonucleotides enclosing the appropriate target sequence SEQ ID NO:3 are synthesized using an ABI DNA synthesizer, one primer being modified to contain a signature sequence. The target sequence SEQ ID NO:3 is amplified in a standard PCR reaction optimized for the particular target sequence and its primers. Thermal cycling is performed in a Perkin Elmer thermal cycler, model 9600 or 2400 as follows: 35 cyles of 90° C. for 30 seconds, 55° C. for 30 seconds and 72° C. for 30 seconds.

The amplified target sequence SEQ ID NO:3 is purified for ligation using the Wizard PCR Prep DNA Purification System by Promega. The manufacturer's protocol for direct purification from PCR reactions is followed, with or with out a vacuum manifold. Quantitation of the target sequence SEQ ID NO:3 is determined by ethidium bromide ladder on an ultrviolet transilluminator, gel electrophoresis with a DNA Mass ladder, or by the Gene Quant II spectrophotometer (Pharmacia).

Ligation of the target sequence SEQ ID NO:3 is done with the pGEM-T Vector System (Promega) following the manufacturer's protocol. The ligation product is prepared for electroporation transformation by ammonium precipitation. To each 10 µl ligation reaction is added 1 µl glycogen, 5 µl 7.5 M ammonium acetate, and 30 µl 100% ethanol. The tube contents are mixed by vortexing and placed at −70° C. for 10 minutes. The tubes are then centrifuged for 10 minutes in a microcentrifuge at more than 3000 but less than 10,000×g. Following centrifugation, the supernatant is decanted and the tube rim blotted briefly. Fifty µl of 70% ethanol is added to the pellet and the tube is centrifuged for 5 minutes in a microcentrifuge at more than 3000 but less than 10,000×g. The supernatant is again decanted, the residual ethanol removed from the sides of the tube, and the tube contents allowed to air dry. Alternatively, the decanted tubes can be centrifuged in a vacuum centrifuge for 5 minutes to remove the residual ethanol. The pellet is resuspended in deionized water to the original volume.

Electrocompetent cells, TOP10F! or JM109, are transformed with the ammonium-precipitated ligation product by electroporation using an Electroporator II (Invitrogen). Forty µl aliquots of electrocompetent cells are placed on ice and 1 µl of the DNA is added. The entire sample volume is transferred, avoiding bubbles, into a chilled electroporation cuvette. The capped cuvette is placed in the electoporator, pulsed, and immediately removed. S.O.C.™ media (Life Technologies) is added (950 ml) and mixed by pipetting one time. The sample is transferred to 17×100 sterile tubes and shaken for 1 hour at 37° C. to allow expression of the antibiotic resistance gene. The sample is plated for colony separation by pipetting 100 µl of the culture onto an LB/ampicillin/5-bromo-3-indolyl/isopropyl beta-D-thiogalactopyranoside (Bluo-gal/IPTG) plate (Sigma).

Recombinant colonies obtained using the pGEM-T Vector system are white. Colonies are screened for the insert by transferring a portion of a white colony into the appropriate PCR mix. Amplification is performed according to the original protocol used to obtain the insert. Presence of a PCR product of the expected size is confirmed by electrophoresis on a 6% polyacrylamide gel. The PCR product is then probed for the target sequence SEQ ID NO:3 by dot blot hybridization, using alkaline phosphatase-labeled oligonucleotides as described in Example 1. For example, Leiden Factor V PCR product is applied to a strip of Oncor membrane. The membrane is briefly treated with 0.2 N NaOH and then blocked with blocking buffer (0.2% I-Block by Tropix, 10× PBS, 10% sodium dodecyl sulfate). The appropriate Leiden Factor V probe (mutant or wild type), synthesized as previously described, is diluted in blocking buffer and incubated with the membrane at 53° C. for 30 minutes. Excess probe is removed from the membrane by washing twice for 5 minutes each with 0.5% SDS in PBS. The membrane is then prepared for staining by two 5-minute incubations in a solution of 1 mM $MgCl_2$, 0.1M diethylamine. The substrate, CSPD by Tropix, is pipetted onto the membrane. After 5 minutes the CSPD is removed and the membrane is air dried. The membrane is wrapped in plastic and exposed to a film for 10–30 minutes.

Clones containing the target sequence SEQ ID NO:3 are grown overnight in LB/ampicillin broth. The resultant culture is separated into aliquots, mixed with glycerol to 15–50%, and frozen in aliquots at −70° C.

For preparation of the control material, frozen clones containing the target sequence SEQ ID NO:3 are grown overnight in 3 ml LB/ampicillin broth. A 1:100 dilution of the culture is made by pipetting 0.2 ml of the O/N into 20 ml of LB/ampicillin broth. The sample is incubated on a shaker at 37° C. for several hours until late log phase growth is acheived. The culture is centrifuged for 20 minutes at more than 3000 but less than 10,000×g and the supernatant is decanted. The pelleted cells are resuspended in 20 ml of buffered 10% formalin and incubated at room temperature for a minimum of 2 hours. The cells are again pelleted and washed with 20 ml of PBS, pH 7.4. The washed cell pellet is resuspended in PBS to a concentration appropriate for the assay in which the control is to be used. Cells containing the Factor V sequence SEQ ID NO:3 are diluted with PBS to an optical density at 600 nm ($OD_{600}$)=0.300. Working solutions of the control material are made by diluting the PBS cell suspensions with 0.017 M imidazole/NaCl, pH 7.4.

EXAMPLE 4

Target sequences for *Chlamydia trachomatis* are determined from the literature or empirically using various techniques known to one skilled in the art including PCR, gel electrophoresis, and sequencing. Oligonucleotides enclosing the appropriate target sequence SEQ ID NO:4 are synthesized using an ABI DNA synthesizer, one primer being modified to contain a signature sequence. The target sequence SEQ ID NO:4 is amplified in a standard PCR reaction optimized for the particular target sequence and its primers. Thermal cycling is performed in a Perkin Elmer thermal cycler, model 9600 or 2400 as follows: 30 cyles of 94° C. for 30 seconds, 50° C. for 30 seconds and 72° C. for 30 seconds.

The amplified target sequence SEQ ID NO:4 is purified for ligation using the Wizard PCR Prep DNA Purification System by Promega. The manufacturer's protocol for direct purification from PCR reactions is followed, with or with out a vacuum manifold. Quantitation of the target sequence SEQ ID NO:4 is determined by ethidium bromide ladder on an ultraviolet transilluminator, gel electrophoresis with a DNA Mass ladder, or by the Gene Quant II spectrophotometer (Pharmacia).

Ligation of the target sequence SEQ ID NO:4 is done with the pGEM-T Vector System (Promega) using the manufacturer's protocol. The ligation product is prepared for electroporation transformation by ammonium precipitation. To each 10 µl ligation reaction is added 1 µl glycogen, 5 µl 7.5 M ammonium acetate, and 30 µl 100% ethanol. The tube contents are mixed by vortexing and placed at −70° C. for 10 minutes. The tubes are then centrifuged for 10 minutes in a microcentrifuge at more than 3000 but less than 10,000×g. Following centrifugation, the supernatant is decanted and the tube rim blotted briefly. Fifty µl of 70% ethanol is added to the pellet and the tube is centrifuged for 5 minutes in a microcentrifuge at more than 3000 but less than 10,000×g. The supernatant is again decanted, the residual ethanol removed from the sides of the tube, and the tube contents allowed to air dry. Alternatively, the decanted tubes can be centrifuged in a vacuum centrifuge for 5 minutes to remove the residual ethanol. The pellet is resuspended in deionized water to the original volume.

Electrocompetent cells, TOP10F! or JM109, are transformed with the ammonium precipitated ligation product by electroporation using an Electroporator II (Invitrogen). Forty µl aliquots of electrocompetent cells are placed on ice and 1 µl of the DNA preparation is added. The entire sample volume is transferred, avoiding bubbles, into a chilled electroporation cuvette. The capped cuvette is placed in the electoporator, pulsed, and immediately removed. S.O.C.™ media (Life Technologies) is added (950 ml) and mixed by pipetting one time. The sample is transferred to 17×100 sterile tubes and shaken for 1 hour at 37° to allow expression of the antibiotic resistance gene. The sample is plated for colony separation by pipetting 100 µl of the culture onto an LB/ampicillin/5-bromo-3-indolyl/isopropyl beta-D-thiogalactopyranoside (bluo-gal/IPTG) plate (Sigma). Recombinant colonies obtained using the pGEM-T Vector system are white. Colonies are screened for the insert by transferring a portion of a white colony into the appropriate PCR mix. Amplification is performed according to the original protocol used to obtain the insert. The presence of a PCR product of the expected size is confirmed by electrophoresis on a 6% polyacrylamide gel with subsequent ethidium bromide staining. A portion of a recombinant colony is also transferred with an inoculating loop into an Abbott LCx specimen collection tube containing transport buffer. The tube is then processed according to the Abbott protocol, beginning with the swab specimen preparation step of heating the tube in a 97° C. dry bath for 15 minutes.

Clones containing the target sequence SEQ ID NO:4 are propagated by growing each clone overnight in LB/ampicillin broth. The culture is mixed with glycerol to 15–50% and frozen in aliquots at −70° C.

Control materials are produced by removal of aliquots of the frozen clones containing the target sequence SEQ ID NO:4 and growing overnight in 3 ml of LB/ampicillin broth. A 1:100 dilution of the culture is made by pipetting 0.2 ml of the O/N culture into 20 ml of LB/ampicillin broth. The mixture is incubated on a shaker at 37° C. for several hours until late log phase growth is acheived. The culture is centrifuged 20 minutes at more than 3000 but less than 10,000×g and the supernatant is decanted. The pelleted cells are resuspended in 20 ml of buffered 10% formalin and incubated at room temperature for a minimum of 2 hours. The cells are again pelleted and washed with 20 ml of PBS, pH 7.4. The washed cell pellet is resuspended in PBS to a concentration appropriate for the assay in which the control is to be used. For example, the cells containing the *Chlamydia trachomatis* plasmid sequence SEQ ID NO:4 are diluted with PBS to an optical density at 600 nm ($OD_{600}$)=0.100. ProClin® is added to a concentration of 0.04%. Working solutions of the control material are made by diluting the PBS cell suspensions with 0.017 M imidazole/NaCl, pH 7.4.

EXAMPLE 5

Target sequences for a hereditary hemochromatosis gene are determined from the literature or empirically using various techniques known to one skilled in the art including PCR, gel electrophoresis, and sequencing. Oligonucleotides enclosing the appropriate target sequence SEQ ID NO:5 are synthesized using an ABI DNA synthesizer, one primer being modified to contain a signature sequence. The target sequence SEQ ID NO:5 is amplified in a standard PCR reaction optimized for the particular target sequence and its primers. Thermal cycling is performed in a Perkin Elmer thermal cycler, model 9600 or 2400 as follows: 95° C. for 5 min followed by 40 cycles of 94° C. for 30 seconds, 53° C. for 30 seconds and 72° C. for 30 seconds.

The amplified target sequence SEQ ID NO:5 is purified for ligation using the Wizard PCR Prep DNA Purification System by Promega. The manufacturer's protocol for direct purification from PCR reactions is followed, with or with out a vacuum manifold. Quantitation of the target sequence SEQ ID NO:5 is determined by ethidium bromide ladder on an ultrviolet transilluminator, gel electrophoresis with a DNA Mass ladder, or by the Gene Quant II spectrophotometer (Pharmacia).

Ligation of the target sequence SEQ ID NO:5 is done with the pGEM-T Vector System (Promega) following the manufacturer's protocol. The ligation product is prepared for electroporation transformation by ammonium precipitation. To each 10 μl ligation reaction is added 1 μl glycogen, 5 μl 7.5 M ammonium acetate, and 30 μl 100% ethanol. The tube contents are mixed by vortexing and placed at −70° C. for 10 minutes. The tubes are then centrifuged for 10 minutes in a microcentrifuge at more than 3000 but less than 10,000×g. Following centrifugation, the supernatant is decanted and the tube rim blotted briefly. Fifty μl of 70% ethanol is added to the pellet and the tube is centrifuged for 5 minutes in a microcentrifuge at more than 3000 but less than 10,000×g. The supernatant is again decanted, the residual ethanol removed from the sides of the tube, and the tube contents allowed to air dry. Alternatively, the decanted tubes can be centrifuged in a vacuum centrifuge for 5 minutes to remove the residual ethanol. The pellet is resuspended in deionized water to the original volume.

Electrocompetent cells, TOP10F! or JM109, are transformed with the ammonium-precipitated ligation product by electroporation using an Electroporator II (Invitrogen). Forty μl aliquots of electrocompetent cells are placed on ice and 1 μl of the DNA is added. The entire sample volume is transferred, avoiding bubbles, into a chilled electroporation cuvette. The capped cuvette is placed in the electoporator, pulsed, and immediately removed. S.O.C.™ media (Life Technologies) is added (950 ml) and mixed by pipetting one time. The sample is transferred to 17×100 sterile tubes and shaken for 1 hour at 37° C. to allow expression of the antibiotic resistance gene. The sample is plated for colony separation by pipetting 100 μl of the culture onto an LB/ampicillin/5-bromo-3-indolyl/isopropyl beta-D-thiogalactopyranoside (Bluo-gal/IPTG) plate (Sigma).

Recombinant colonies obtained using the pGEM-T Vector system are white. Colonies are screened for the insert by transferring a portion of a white colony into the appropriate PCR mix. Amplification is performed according to the original protocol used to obtain the insert. Presence of a PCR product of the expected size is confirmed by electrophoresis on a 6% polyacrylamide gel. The PCR product is then probed for the target sequence SEQ ID NO:5 by dot blot hybridization, using alkaline phosphatase-labeled oligonucleotides as described in Example 1. For example, the hereditary hemochromatosis gene PCR product is applied to a strip of Oncor membrane. The membrane is briefly treated with 0.2 N NaOH and then blocked with blocking buffer (0.2% I-Block by Tropix, 10× PBS, 10% sodium dodecyl sulfate). The appropriate hereditary hemochromatosis gene probe (mutant or wild type), synthesized as previously described, is diluted in blocking buffer and incubated with the membrane at 50° C. for 30 minutes. Excess probe is removed from the membrane by washing twice for 5 minutes each with 0.5% SDS in PBS. The membrane is then prepared for staining by two 5-minute incubations in a solution of 1 mM $MgCl_2$, 0.1M diethylamine. The substrate, CSPD by Tropix, is pipetted onto the membrane. After 5 minutes the CSPD is removed and the membrane is air dried. The membrane is wrapped in plastic and exposed to a film for 10–30 minutes.

Clones containing the target sequence SEQ ID NO:5 are grown overnight in LB/ampicillin broth. The resultant culture is separated into aliquots, mixed with glycerol to 15–50%, and frozen in aliquots at −70° C.

For preparation of the control material, frozen clones containing the target sequence SEQ ID NO:5 are grown overnight in 3 ml LB/ampicillin broth. A 1:100 dilution of the culture is made by pipetting 0.2 ml of the O/N into 20 ml of LB/ampicillin broth. The sample is incubated on a shaker at 37° C. for several hours until late log phase growth is achieved. The culture is centrifuged for 20 minutes at more than 3000 but less than 10,000×g and the supernatant is decanted. The pelleted cells are resuspended in 20 ml of buffered 10% formalin and incubated at room temperature for a minimum of 2 hours. The cells are again pelleted and washed with 20 ml of PBS, pH 7.4. The washed cell pellet is resuspended in PBS to a concentration appropriate for the assay in which the control is to be used. Cells containing the hereditary hemochromatosis sequence SEQ ID NO:5 are diluted with PBS to an optical density at 600 nm ($OD_{600}$)= 0.300. Working solutions of the control material are made by diluting the PBS cell suspensions with 0.017 M imidazole/NaCl, pH 7.4.

While the present invention has been illustrated by a description of embodiments and examples, and while the illustrative embodiments have been described in considerable detail, it is not the intention of the inventors to restrict or in any way limit the scope of the appended claims to such detail. Additional advantages and modifications will readily appear to those skilled in the art. For example, different target DNA sequences and different modifications of these sequences may be used. As another example, a different method for acquiring target DNA sequences may be used. As still another example, a different vector delivery system may be used. The invention in its broader aspects is therefore not limited to the specific details, representative apparatus and methods, and illustrative examples shown and described. Accordingly, departures may be made from such details without departing from the spirit or scope of applicant's general inventive concept.

Having described the invention, what is claimed is:

1. A method for biologically preparing a stable encapsulated reference nucleic acid for molecular diagnostic and genetic testing comprising:
   inserting a vector bearing a reference nucleic acid into a cell through its lipoprotein outer membrane to encapsulate the reference nucleic acid;
   propagating the reference nucleic acid by multiplying the cell number;
   causing cell death without affecting the encapsulated reference nucleic acid; and
   achieving a desired stability of the membrane of the cell containing the reference nucleic acid by crosslinking the protein in the membrane under controlled conditions for substantially matching with the membrane stability of the test cells.

2. The method of claim 1 wherein the nucleic acid is an RNA obtained by transcription of a DNA fragment.

3. The method of claim 1 wherein the nucleic acid is a DNA obtained by a method selected from the group consisting of chemical synthesis, cleavage of a genomic DNA sequence, formation of a complementary DNA sequence, and in vitro amplification of a DNA fragment.

4. The method of claim 1 wherein the nucleic acid is a DNA selected from the group consisting of a Parvovirus B-19 SEQ ID NO:1, a lipoprotein lipase gene SEQ ID NO:2, a Leiden Factor V mutant SEQ ID NO:3, a *Chlamydia trachomatis* SEQ ID NO:4, and a hereditary hemochromatosis candidate gene SEQ ID NO:5.

5. The method of claim 1 wherein the vector is selected from the group consisting of a plasmid, a virus and a self-replicating system.

6. The method of claim 5 wherein the plasmid is selected from the group consisting of pBR322 and pGEM-T.

7. The method of claim 5 wherein the virus is a bacteriophage.

8. The method of claim 1 wherein the nucleic acid has a unique signature mutation incorporated therein.

9. The method of claim 8 comprising incorporating a signature mutation using a polymerase chain reaction to incorporate a mutating primer.

10. The method of claim 8 wherein the signature mutation contains a restriction endonuclease cleavage site.

11. The method of claim 8 wherein the signature mutation is detected by a method of analysis selected from the group consisting of size, restriction, sequence, and specific hybridization.

12. The method of claim 1 comprising quantitating a cell number by a method selected from the group consisting of an optical density, a particle counting, and a culture.

13. The method of claim 1 comprising verifying the insertion of the vector bearing the reference nucleic acid into the cell by a method selected from the group consisting of a drug resistance screen, a β-galactosidase activity screen, and a PCR screen.

14. The method of claim 1 comprising causing cell death without affecting the encapsulated reference nucleic acid by a method selected from the group consisting of exposure to ambient temperature, a chemical agent, a chemical crosslinker, a chemical carcinogen, a radiation source, and combinations thereof.

15. The method of claim 14 wherein the chemical agent is selected from the group consisting of hypochlorite, ethanol, glutaraldehyde, formaldehyde, and mixtures thereof.

16. The method of claim 1 comprising crosslinking by adding an agent selected from the group consisting of glutaraldehyde, formaldehyde, disuccinimidyl suberate, and mixtures thereof.

17. The stable encapsulated reference nucleic acid produced by the method of claim 1.

18. The stable encapsulated reference nucleic acid produced by the method of claim 1 wherein the nucleic acid is selected from the group consisting of an HIV diagnostic sequence, an HCV diagnostic sequence, a Parvovirus B-19 SEQ ID NO:1, a lipoprotein lipase gene SEQ ID NO:2, a Leiden Factor V mutant SEQ ID NO:3, a *Chlamydia trachomatis* SEQ ID NO:4, and a hereditary hemochromatosis candidate gene SEQ ID NO:5.

19. The stable encapsulated reference nucleic acid produced by the method of claim 1 in a form selected from the group consisting of a solid and a liquid.

20. The stable encapsulated reference nucleic acid produced by the method of claim 1 being contained on a solid support.

21. The stable encapsulated reference nucleic acid produced by the method of claim 1 wherein the nucleic acid is stable when stored at ambient temperature.

22. A method for biologically preparing a class of stable encapsulated reference DNAs for molecular diagnostic and genetic testing of test cells comprising:
   inserting a vector selected from the group consisting of:
      (i) a first vector bearing a reference DNA and a second identical vector bearing a second nonidentical reference DNA,
      (ii) a first vector bearing a reference DNA and a second nonidentical vector bearing a second nonidentical reference DNA, and
      (iii) a vector bearing at least two nonidentical reference DNAs, into a cell through a lipoprotein outer membrane of the cell to encapsulate the reference DNAs;
   propagating the reference DNA by multiplying the cell number:
   causing cell death without affecting the encapsulated reference DNA; and
   achieving a desired stability of the membrane of the cell containing the reference DNA by crosslinking the protein in the membrane under control for substantially matching with the membrane stability of the test cells.

23. The method of claim 22(i) wherein the number of identical vectors per cell is from about one to about one thousand.

24. The method of claim 22(ii) wherein the number of nonidentical vectors per cell is from about two to about four.

25. The method of claim 22(iii) wherein the number of nonidentical reference DNAs per vector is from about two to about twenty.

26. A method of biologically preparing a stable encapsulated reference DNA for molecular diagnostic and genetic testing of test cells comprising:
   inserting a plasmid bearing a reference DNA containing a signature mutation into an *E. coli* bacterium through its lipoprotein cell wall to encapsulate the reference DNA;
   propagating the reference DNA by multiplying the cell number;
   causing bacterial death without affecting the encapsulated reference DNA; and
   achieving a desired stability of the membrane of the cell containing the reference DNA by crosslinking the protein in the membrane under control for substantially matching with the membrane stability of the test cells.

27. The method of claim 26 comprising causing cell death without affecting the encapsulated reference nucleic acid by a method selected from the group consisting of exposure to ambient temperature, a chemical agent, a chemical crosslinker, a chemical carcinogen, a radiation source, and combinations thereof.

28. The method of claim 27 wherein the chemical agent is selected from the group consisting of hypochlorite, ethanol, glutaraldehyde, formaldehyde, and mixtures thereof.

29. The method of claim 26 comprising crosslinking by adding an agent selected from the group consisting of glutaraldehyde, formaldehyde, disuccinimidyl suberate, and mixtures thereof.

30. The method of claim 26 comprising using DNA selected from the group consisting of a Parvovirus B-19 SEQ ID NO:1, a lipoprotein lipase gene SEQ ID NO:2, a Leiden Factor V mutant SEQ ID NO:3, a *Chlamydia trachomatis* SEQ ID NO:4, and a hereditary hemochromatosis gene SEQ ID NO:5.

31. A method for preparing a stable encapsulated reference DNA for molecular diagnostic and genetic testing of test cells comprising
   inserting a reference DNA into a vehicle through its outer membrane to encapsulate the reference DNA;
   altering the membrane without affecting the encapsulated reference DNA; and
   achieving a desired stability of the membrane of the vehicle containing the reference DNA by crosslinking the protein in the membrane under control for substantially matching with the membrane stability of the test cells.

32. The method of claim 31 wherein the vehicle is selected from the group consisting of an agarose capsule and a liposome.

33. The method of claim 31 comprising using DNA obtained by a method selected from the group consisting of chemical synthesis, cleavage of a genomic DNA sequence, formation of a complementary DNA sequence, and in vitro amplification of a DNA fragment.

34. The method of claim 31 comprising using DNA selected from the group consisting of a Parvovirus B-19 SEQ ID NO:1, a lipoprotein lipase gene SEQ ID NO:2, a Leiden Factor V mutant SEQ ID NO:3, a *Chlamydia trachomatis* SEQ ID NO:4, and a hereditary hemochromatosis candidate gene SEQ ID NO:5.

35. The method of claim 31 wherein the DNA has a signature mutation incorporated therein.

36. The method of claim 35 comprising incorporating a signature mutation using the polymerase chain reaction to incorporate a mutating primer.

37. The method of claim 35 wherein the signature mutation contains a restriction endonuclease cleavage site.

38. The method of claim 35 wherein the signature mutation is detected by a method of analysis selected from the group consisting of DNA size, DNA restriction, DNA sequence, and allele specific hybridization.

39. The method of claim 36 comprising crosslinking by adding an agent selected from the group consisting of glutaraldehyde, formaldehyde, disuccinimidyl suberate, and mixtures thereof.

* * * * *

UNITED STATES PATENT AND TRADEMARK OFFICE
CERTIFICATE OF CORRECTION

PATENT NO. : 5,994,078
DATED : November 30, 1999
INVENTOR(S) : Rundell, Clark A. and Vart, Calvin P.H.

It is certified that error appears in the above-identified patent and that said Letters Patent is hereby corrected as shown below:

Column 20,
Line 56, change "36" to -- 31 --.

Signed and Sealed this

Sixth Day of November, 2001

Attest:

*Nicholas P. Godici*

NICHOLAS P. GODICI
*Attesting Officer*     *Acting Director of the United States Patent and Trademark Office*